United States Patent
Nishijima (10) Patent No.: US 9,702,836 B2
(45) Date of Patent: Jul. 11, 2017

(54) PM DETECTION APPARATUS

(75) Inventor: Hiroki Nishijima, Suntou-gun (JP)

(73) Assignee: TOYOTA JIDOSHA KABUSHIKI KAISHA, Toyota-shi (JP)

(*) Notice: Subject to any disclaimer, the term of this patent is extended or adjusted under 35 U.S.C. 154(b) by 443 days.

(21) Appl. No.: 13/818,227

(22) PCT Filed: Sep. 8, 2010

(86) PCT No.: PCT/JP2010/065420
§ 371 (c)(1),
(2), (4) Date: Feb. 21, 2013

(87) PCT Pub. No.: WO2012/032622
PCT Pub. Date: Mar. 15, 2012

(65) Prior Publication Data
US 2013/0145815 A1  Jun. 13, 2013

(51) Int. Cl.
*G01N 25/00* (2006.01)
*F02D 41/14* (2006.01)
(Continued)

(52) U.S. Cl.
CPC .......... *G01N 25/00* (2013.01); *F02D 41/1446* (2013.01); *F02D 41/1466* (2013.01);
(Continued)

(58) Field of Classification Search
CPC ...................................................... G01N 25/00
(Continued)

(56) References Cited

U.S. PATENT DOCUMENTS 6,202,469 B1    3/2001  Nakamura et al.
2002/0060992 A1*  5/2002  Endo ............... 370/310
(Continued)

FOREIGN PATENT DOCUMENTS

JP      10 177005       6/1998
JP      2005 248760     9/2005
(Continued)

OTHER PUBLICATIONS

English Translation of JP 2005-248760, Sep. 15, 2005.*
International Search Report Issued Nov. 22, 2010 in PCT/JP10/65420 Filed Sep. 8, 2010.

*Primary Examiner* — Michael A Lyons
*Assistant Examiner* — Alexander Mercado
(74) *Attorney, Agent, or Firm* — Oblon, McClelland, Maier & Neustadt, L.L.P.

(57) ABSTRACT

An object of the present invention is to reliably detect clogging in a cover even during a period corresponding to a dead zone of a detection apparatus. A PM sensor includes an element section, an element temperature detection section, a heater, and an element cover. An ECU detects clogging in the element cover based on a difference between an element temperature and an exhaust temperature when the exhaust temperature rises. Furthermore, the ECU detects clogging in the element cover based on temperature rising characteristics of the element section observed when the element section is heated by the heater. Thus, even during the period corresponding to the dead zone of the PM sensor, clogging in the element cover can be reliably detected, thus improving the reliability of the sensor.

9 Claims, 5 Drawing Sheets

(51) Int. Cl.
*F02D 41/22* (2006.01)
*G01N 15/06* (2006.01)
*G01N 27/04* (2006.01)

(52) U.S. Cl.
CPC ..... *F02D 41/1494* (2013.01); *F02D 41/1495* (2013.01); *F02D 41/222* (2013.01); *G01N 15/0656* (2013.01); *F01N 2560/05* (2013.01); *F02D 41/1496* (2013.01); *G01N 27/04* (2013.01); *Y02T 10/40* (2013.01)

(58) Field of Classification Search
USPC .................................. 73/1.06, 23.33, 28.01
See application file for complete search history.

(56) References Cited

U.S. PATENT DOCUMENTS

| | | | |
|---|---|---|---|
| 2009/0051376 A1 | 2/2009 | Schnell et al. | |
| 2010/0018186 A1* | 1/2010 | Shibata et al. | 60/277 |
| 2011/0186093 A1* | 8/2011 | Publ et al. | 134/109 |
| 2011/0301908 A1* | 12/2011 | Magarida | 702/130 |

FOREIGN PATENT DOCUMENTS

| | | |
|---|---|---|
| JP | 2008 502892 | 1/2008 |
| WO | WO 03006976 A2 * | 1/2003 |

\* cited by examiner

PM DETECTION APPARATUS

TECHNICAL FIELD

The present invention relates to a PM detection apparatus preferably used to detect particulate matter (PM) in exhaust gas.

BACKGROUND ART

As a conventional technique, a gas concentration detection apparatus configured to detect the concentration of oxygen in exhaust gas or the like is known as disclosed in, for example, Patent Literature 1 (Japanese Patent Laid-Open No. 10-177005). The gas concentration detection apparatus according to the conventional technique includes a detection element arranged in an exhaust passage in an engine. The detection element is covered with a double cylinder-like sensor cover provided with a plurality of vent holes. The sensor cover has a function to protect the detection element and a function to stabilize a flow of exhaust gas which comes into contact with the detection element.

Furthermore, as another conventional technique, a PM sensor is known which detects the amount of PM contained in exhaust gas. The PM sensor according to the conventional technique includes two electrodes arranged opposite each other in an exhaust passage. The PM sensor is configured to detect the amount of PM in the exhaust gas utilizing the value of the resistance between the electrodes varying depending on the amount of PM accumulated between the electrodes. Furthermore, the PM sensor includes a sensor cover which covers an area where the electrodes are arranged. The sensor cover has a structure and functions similar to the structure and functions of the sensor cover of the above-described gas concentration detection apparatus.

CITATION LIST

Patent Literature

Patent Literature 1: Japanese Patent Laid-Open No. 10-177005

SUMMARY OF INVENTION

Technical Problem

The PM sensor according to the conventional technique detects the amount of PM based on a change in the value of the resistance between the electrodes. Thus, the PM sensor fails to detect the amount of PM when a sufficient amount of PM to form an electrically conductive path between the electrodes has not accumulated, as in the case of an initial state of the sensor. That is, the period from the initial state until a conductive path is formed between the electrodes corresponds to a dead zone in which the PM sensor is non-functional. On the other hand, in the PM sensor, the vent holes in the sensor cover may be clogged with components of the exhaust gas or the like. This degrades the functions of the sensor. However, during the period corresponding to the dead zone of the sensor, even if the sensor cover is subjected to clogging, the degradation of the functions of the sensor caused by the clogging cannot be detected. This disadvantageously reduces reliability.

The present invention solves the above-described problems. An object of the present invention is to provide a PM detection apparatus which can reliably detect clogging in the cover even during the period corresponding to the dead zone, thus improving reliability.

Means for Solving the Problem

A first aspect of the present invention is a PM detection apparatus, comprising:
an element section comprising at least two electrodes arranged opposite each other in a channel for exhaust gas, the element section being configured such that particulate matter in exhaust gas accumulates between the electrodes;
a detection processing section detecting an amount of the particulate matter contained in the exhaust gas based on a change in a value of resistance between the electrodes;
an element cover formed as a cover with a vent hole and covering the element section;
element temperature detection means for detecting a temperature of the element section; and
clogging detection means for detecting when the vent hole in the element cover is clogged based on the temperature of the element section.

In a second aspect of the present invention, the PM detection apparatus comprising exhaust temperature detection means for detecting an exhaust temperature on an upstream side of the element section, wherein
the clogging detection means is configured to determine that the element cover is subjected to clogging if a difference between the temperature of the element section and the exhaust temperature is greater than a predetermined judgment value.

In a third aspect of the present invention, the PM detection apparatus comprising a heater heating the element section, wherein
the clogging detection means is configured to measure an elapsed time from start of heating of the element section by the heater until the temperature of the element section reaches a predetermined reference temperature and to determine that the element cover is subjected to clogging if the elapsed time is shorter than a predetermined judgment time.

In a fourth aspect of the present invention, the PM detection apparatus comprising a heater heating the element section, wherein
the clogging detection means is configured to determine that the element cover is subjected to clogging if a change in the temperature of the element section observed when the element section is heated by the heater is greater than a predetermined judgment value.

In a fifth aspect of the present invention, the PM detection apparatus comprising:
cover heating means for enabling the element cover to be heated; and
clogging elimination means for allowing the cover heating means to heat the element cover to eliminate clogging if the clogging detection means detects that the element cover is subjected to clogging.

Advantageous Effects of Invention

According to a first aspect of the invention, the clogging detection means can detect when the vent hole in the element cover is clogged based on the temperature of an element section. This allows the appropriate processing for the clogging in the element cover to be carried out. Furthermore, since the clogging is detected using the temperature of the element section, the detection can be reliably achieved even during the period corresponding to the dead zone of the PM detection apparatus. Therefore, reliability can be improved.

According to a second aspect of the invention, the temperature of the element section rises following an increase in the temperature of the exhaust gas flowing in through the vent hole in the element cover. Thus, if the element cover is subjected to clogging, the temperature of the element section fails to follow the exhaust temperature. Therefore, the clogging detection means can determine that the element cover is subjected to clogging if the difference between the temperature of the element section and the exhaust temperature is greater than the judgment value.

According to a third aspect of the invention, if the element cover is subjected to clogging, heat from the heater has difficulty escaping to the outside of the element cover. Thus, the element section is efficiently heated. Therefore, the clogging detection means can determine that the element cover is subjected to clogging if the elapsed time from the start of heating until the temperature of the element section reaches the reference temperature is shorter than the judgment time.

According to a fourth aspect of the invention, if the element cover is subjected to clogging, the speed at which the element temperature rises or the rate at which the element temperature changes is higher than in a normal state. Thus, the clogging detection means can determine that the element cover is subjected to clogging if the change in the temperature of the element section observed when the element section is heated is greater than the judgment value.

According to a fifth aspect of the invention, the clogging elimination means allows the cover heating means to heat the element cover if the element cover is subjected to clogging. Thus, the clogging can be quickly eliminated, allowing the functions of the PM detection apparatus to be recovered. Furthermore, if a heater configured to heat the element section is used as the cover heating means, the structure of the PM detection apparatus can be simplified. This also allows simultaneous, efficient execution of a process of combusting PM accumulated in the element section and a process of heating the element cover.

DESCRIPTION OF EMBODIMENTS

Embodiment 1

Configuration of Embodiment 1

Figure 1:
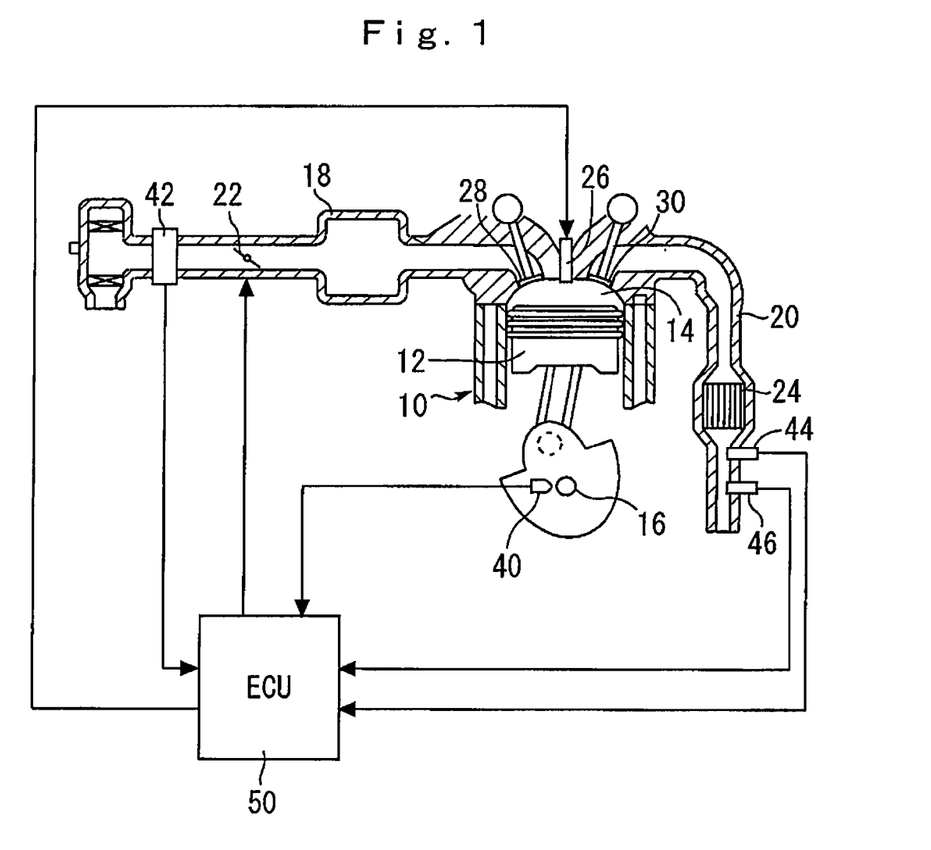
FIG. 1 is a general schematic diagram illustrating the system configuration of Embodiment 1 of the present invention.

Hereinafter, Embodiment 1 of the present invention will be described with reference to FIG. 1 to FIG. 7. FIG. 1 is a general schematic diagram illustrating the system configuration of Embodiment 1 of the present invention. The system of the present embodiment includes an engine 10 formed of, for example, a diesel engine. Each cylinder of the engine 10 includes a combustion chamber 14 formed by a piston 12 coupled to a crank shaft 16 of the engine. Furthermore, the engine 10 includes an intake passage 18 through which intake air is sucked into the each cylinder and an exhaust passage 20 through which exhaust gas from each cylinder is discharged. The intake passage 18 is provided with an electronic-controlled throttle valve 22 which adjusts the amount of intake air. Additionally, the exhaust passage 20 is provided with a DPF (Diesel Particulate Filter) 24 which collects particulate matter (PM) contained in exhaust gas, and various catalysts (not shown in the drawings) which purify exhaust gas. In addition, each cylinder includes a fuel injection valve 26, a suction valve 28, and an exhaust valve 30.

Furthermore, the system according to the present embodiment includes a sensor system with sensors 40, 42, 44, and 46 and an ECU (Electronic Control Unit) 50 which controls the operating state of the engine 10. First, the sensor system will be described. The crank angle sensor 40 outputs a signal which synchronizes with rotation of the crank shaft 16. The air flow sensor 42 detects the amount of air sucked into the engine. Furthermore, the exhaust temperature sensor 44 detects exhaust temperature on an upstream side of the PM sensor 46 and forms exhaust temperature detection means according to the present embodiment. The PM sensor 46 detects the amount of PM contained in the exhaust gas and is configured as described below.

Furthermore, the sensor system includes various sensors required to control the engine 10 and a vehicle with the engine 10 mounted thereon (for example, a water temperature sensor which detects, for example, the temperature of an engine coolant, and an air-to-fuel ratio sensor which detects the air-to-fuel ratio of exhaust). These sensors are connected to an input side of the ECU 50. On the other hand, an output side of the ECU 50 connects to various actuators such as the throttle valve 22 and the fuel injection valve 26.

The ECU 50 controls operation by driving the actuators based on operation information on the engine detected by the sensor system. Specifically, the ECU 50 detects engine rotating speed and crank angle based on an output from the crank angle sensor 40. The ECU 50 allows the air flow sensor 42 to detect intake air volume. Furthermore, the ECU 50 calculates the amount of injected fuel based on the intake air volume, the engine rotating speed, and the like and determines the time to inject fuel based on the crank angle. At the time to inject fuel, the ECU 50 drives the fuel injection valve 26. Thus, the ECU 50 enables an air-fuel mixture to be combusted in the combustion chamber 14 of each cylinder to operate the engine 10.

Figure 2:
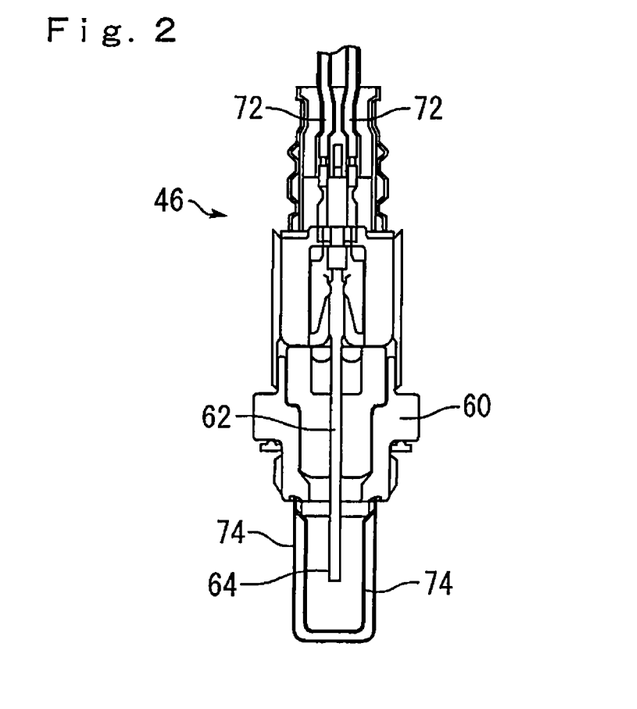
FIG. 2 is a cross-sectional view of the PM sensor.

Now, with reference to FIG. 2, the structure of the PM sensor 46 will be described. FIG. 2 is a cross-sectional view of the PM sensor. As shown in FIG. 2, the PM sensor 46 includes a housing 60, an element section 64, an element cover 74, and the like, and has a well-known configuration. The housing 60 is generally formed like a stepped cylinder using a plurality of components, with a rod-like element support section 62 inserted into an inner peripheral side of the housing 60. The element support section 62 is formed of, for example, an insulating ceramics material or a resin material. A leading end side of the element support section 62 projects from the housing 60 in an axial direction.

Figure 3:
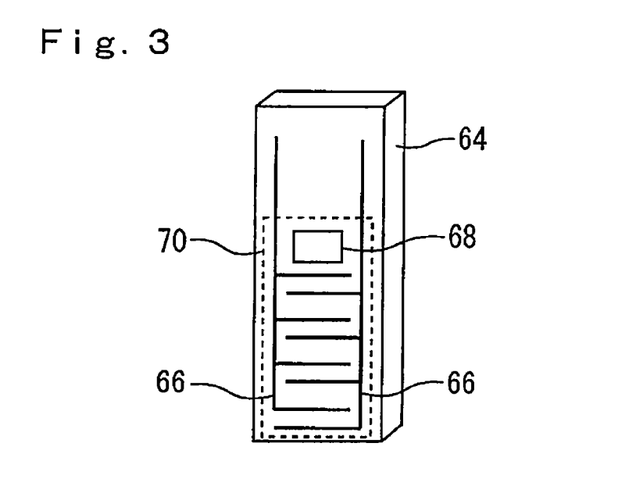
FIG. 3 is an enlarged view showing the appearance of the element section of the PM sensor.

The element section 64, which forms a detection section of the PM sensor 46, is provided on the leading end side of the element support section 62. As shown in FIG. 3 described below, the element section 64 includes electrodes 66, 66, an element temperature detection section 68, and a heater 70 arranged thereon. The electrodes 66, 66, element temperature detection section 68, and heater 70 are connected to the ECU 50 via a plurality of wires 72 or the like. The element section 64 may be integrated with element support section 62. Furthermore, with the PM sensor 46 installed in the exhaust passage 20, the element section 64 is exposed in a channel for exhaust gas. Thus, on a leading end side of the housing 60, double cylinder-like element covers 74, 74 which cover the element section 64 are provided. The element cover 74 is formed like a cylinder with its leading end side occluded. The element cover 74 includes a plurality of vent holes (not shown in the drawings) through which the inside and outside of the element cover 74 communicate with each other. The element cover 74 has a function to introduce exhaust gas into the cover via the vent holes to protect the element section 64 and to stabilize the flow of exhaust gas around the element section 64.

Now, the structure of the element section will be described with reference to FIG. 3. FIG. 3 is an enlarged view showing the appearance of the element section of the PM sensor. As shown in FIG. 3, the two electrodes 66, 66, the element temperature detection section 68, and the heater 70 are arranged in the element section 64. The electrode 66 includes comb-teeth-like shape patterns formed of, for example, a thin-film-like metal material and arranged on a surface of the element section 64 so as to engage with one another. Thus, the two electrodes 66 lie opposite each other on the surface of the element section 64 with a predetermined distance between the electrodes 66. The electrodes 66 are configured so that PM in the exhaust gas accumulates between the electrodes 66. Furthermore, the element temperature detection section 68 detects the temperature of the element section 64 (electrode 66) and outputs a detection signal to the ECU 50. The element temperature detection section 68 forms element temperature detection unit according to the present embodiment. Additionally, the heater 70 is embedded in the element section 64, for example, at a position corresponding to the electrodes 66. The heater 70 is turned on by the ECU 50 to heat the element section 64 (electrode 66). The heater 70 forms cover heating means according to the present embodiment.

Now, the operation of the PM sensor 46 will be described. During operation of the engine, part of the exhaust gas flowing through the exhaust passage 20 flows through the vent holes in the element cover 74 to the periphery of the element section 64. Thus, PM in the exhaust gas gradually accumulates between the electrodes 66 to vary the value of the resistance between the electrodes depending on the amount of accumulated PM. At this time, the amount of accumulated PM increases consistently with the amount of PM contained in the exhaust gas. Thus, the ECU 50 can detect the amount of PM in the exhaust gas based on a change in the value of the resistance between the electrodes 66. The ECU 50 forms a detection processing section according to the present embodiment. On the other hand, the ECU 50 carries out a PM combustion process if at least a given amount of PM accumulates between the electrodes 66. In the PM combustion process, the heater 70 is turned on to combust the PM accumulated between the electrodes 66. Thus, the accumulated PM can be removed, allowing the PM sensor to be recovered to its initial state.

Features of Embodiment 1
(Process of Detecting Clogging in the Element Cover)

As described above, the PM sensor 46 detects the amount of PM based on a change in the value of the resistance between the electrodes 66. Thus, when a sufficient amount of PM to form an electrically conductive path between the electrodes 66 has not been accumulated as in the case of the initial state of the sensor, the output from the sensor does not change even with accumulated PM. This precludes the amount of PM from being detected. That is, the period from the initial state until a conductive path is formed between the electrodes 66 corresponds to a dead zone where the PM sensor 46 is non-functional. On the other hand, the vent holes in the element cover 74 may be clogged with components of exhaust gas or the like. In this case, the functions of the sensor are degraded. However, during the period corresponding to the sensor dead zone, possible clogging in the element cover 74 cannot be detected.

Figure 4:
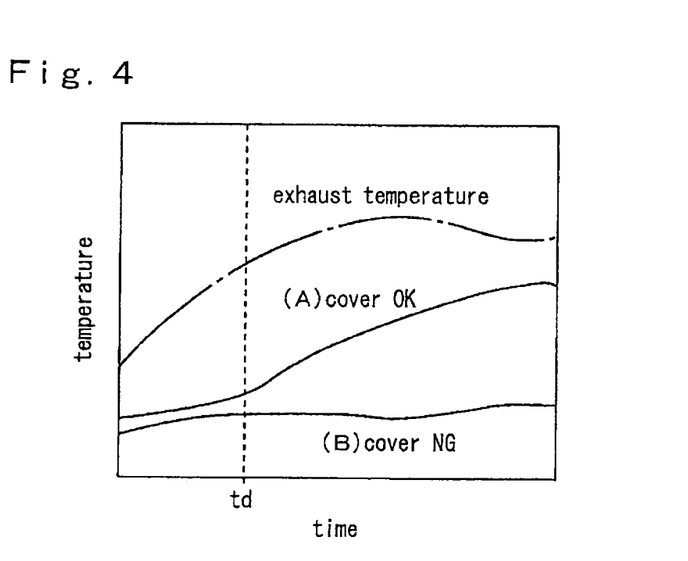
FIG. 4 is a characteristic diagram showing a temporal variation between the exhaust temperature and the element temperature.

Thus, the present embodiment is configured to detect the clogging in the element cover 74 based on the temperature of the element section 64 or the electrodes 66 (hereinafter referred to as the element temperature). Specifically, in a first clogging detection process, the present embodiment determines that the element cover 74 is subjected to clogging if, at the timing when the exhaust temperature rises, the difference between the element temperature and the exhaust temperature is greater than a predetermined judgment value. Here, FIG. 4 is a characteristic diagram showing a temporal variation between the exhaust temperature and the element temperature. A characteristic line (A) in FIG. 4 indicates that the element cover 74 is not subjected to clogging (cover OK). A characteristic line (B) in FIG. 4 indicates that the element cover 74 is subjected to clogging (cover NG).

The element section 64 is heated by exhaust gas flowing in through the vent holes in the element cover 74. Thus, if the element cover 74 is not subjected to clogging, when the exhaust temperature increases, the element temperature rises quickly following the increase in the exhaust temperature as shown by the characteristic line (A). As a result, the difference between the element temperature and the exhaust temperature is relatively small. On the other hand, if the element cover 74 is subjected to clogging, the exhaust gas has difficulty flowing into the element cover 74. This reduces the efficiency with which the element section 64 is heated by the exhaust gas. As a result, the element temperature does not follow the exhaust temperature and is restrained from rising compared to the exhaust temperature or fails to increase, as shown by the characteristic line (B). Therefore, in this case, the difference between the element temperature and the exhaust temperature has a large value.

Based on such a principle, the judgment value is set to a value enabling determination of whether the difference between the element temperature and the exhaust temperature is a difference observed when clogging has occurred or a difference observed when no clogging has occurred. The value is pre-stored in the ECU 50. The ECU 50 calculates the difference between the element temperature and the exhaust temperature based on the output from the exhaust temperature sensor 44 and the output from the element temperature detection section 68. Then, if the difference is larger than the judgment value, the ECU 50 can determine that the element cover 74 is subjected to clogging. Furthermore, if the difference between the element temperature and the exhaust temperature is equal to or smaller than the judgment value, the ECU 50 can determine that no clogging has occurred. This allows the appropriate processing for the clogging in the element cover 74 to be carried out. Furthermore, since the temperature of the element section 64 is used to detect clogging, the clogging can be reliably detected for example, even during the period corresponding to the dead zone of the PM sensor 46. As a result, the reliability of the sensor can be improved.

The above-described clogging detection process is preferably carried out when the element section 64 has a relatively low temperature, for example, when the engine is started. Furthermore, the illustrated configuration determines whether or not clogging has occurred based on the difference between the element temperature and the exhaust temperature. However, the present invention is not limited to this configuration. For example, the determination may be made based on the amounts of change (differential values) in the element temperature and in the exhaust temperature per given time. Specifically, the present invention may calculate the amounts of change in the element temperature and in the exhaust temperature during a given time, and if the difference between the amounts of change exceeds a judgment value, determine that the element cover 74 is subjected to clogging.

(Second Clogging Detection Process)

Figure 5:
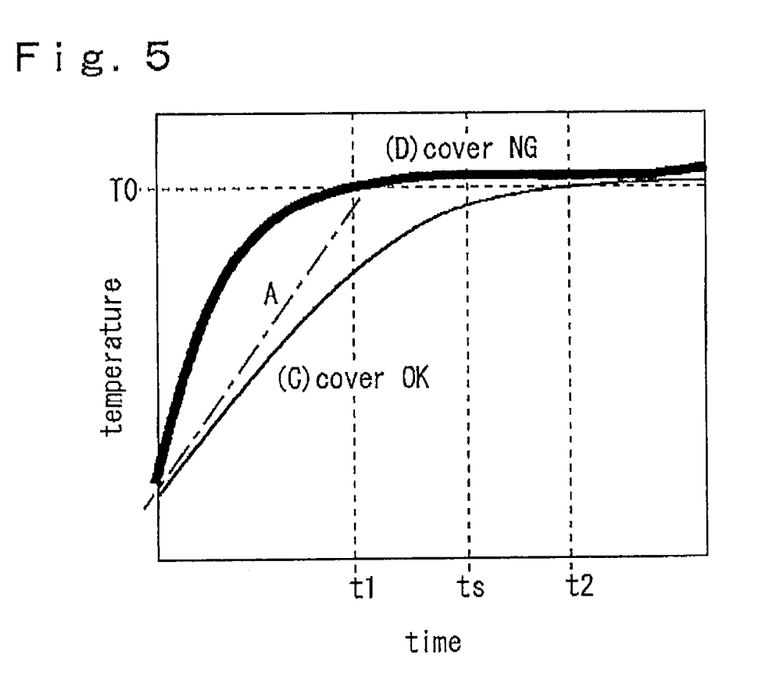
FIG. 5 is a characteristic diagram showing the temperature rising characteristics of the element section observed when the PM combustion process is carried out.

Furthermore, in connection with a second clogging detection process, the present embodiment is configured to, for example, detect clogging based on temperature rising characteristics observed when the element section 64 is heated by a PM combustion process. Specifically, the present embodiment measures the elapsed time t from the start of heating of the element section 64 by the heater 70 until the element temperature reaches a predetermined reference temperature T0 (the elapsed time is hereinafter referred to as a temperature rising time). If the temperature rising time t is shorter than a predetermined judgment time ts, the present embodiment determines that the element cover 74 is subjected to clogging. FIG. 5 is a characteristic diagram showing the temperature rising characteristics of the element section observed when the PM combustion process is carried out. A characteristic line (C) in FIG. 5 indicates that the element cover is not subjected to clogging (cover OK). A characteristic line (D) in FIG. 5 indicates that the element cover is subjected to clogging (cover NG).

If the element cover 74 is subjected to clogging, the space in the cover is shut off from the outside. In this state, when the element section 64 is heated by the heater 70, heat from the heater 70 has difficulty escaping to the outside of the element cover 74. Thus, the element section 64 is efficiently heated. As a result, the element temperature rises quickly as shown by the characteristic line (D). A temperature rising time t1 required for the element temperature to reach a reference temperature T0 is relatively short. On the other hand, if the element cover 74 is not subjected to clogging, heat from the heater 70 escapes to the outside via the vent holes in the element cover 74. Thus, as shown by the characteristic line (C), the element temperature rises relatively slowly, resulting in an extended temperature rising time t2.

Based on such a principle, the judgment time ts is set to a value enabling determination of the temperature rising time, which varies between the different temperature rising times t1 and t2 depending on whether or not clogging has occurred. The value is pre-stored in the ECU 50. Furthermore, the reference temperature T0 is reached by the element section 64 as a result of the PM combustion process and is predetermined. The ECU 50 measures the temperature rising time t required for the element temperature to reach the reference temperature T0 based on the output from the element temperature detection section 68. If the temperature rising time t is shorter than the judgment time ts, the ECU 50 can determine that the element cover 74 is subjected to clogging. Additionally, if the temperature rising time t is equal to or longer than the judgment time ts, the ECU 50 can determine that the element cover 74 is not subjected to clogging. Thus, the second clogging detection process not only can produce advantageous effects similar to those of the first clogging detection process but also allows a clogging detection process to be carried out every time the PM combustion process is executed. This enables an increase in the accuracy with which clogging is detected.

The illustrated configuration determines whether or not clogging has occurred based on the temperature rising time required for the element temperature to reach the reference temperature T0. However, the present invention is not limited to this configuration. The present invention may determine that the element cover 74 is subjected to clogging if for example, the amount of change in the element temperature observed when the element section 64 is heated by the heater 70 (the amount of change is the speed of a rise in the element temperature or the rate of change in the element temperature) is greater than a predetermined judgment value A shown in FIG. 5. That is, if the element cover 74 is subjected to clogging, the speed of a rise in the element temperature or the rate of change in the element temperature is higher than in a normal state, the clogging can also be detected based on the amount of change in the element temperature. This description and the judgement value A is indicative of a specific example of clogging detection unit in the claims.

(Process of Heating the Cover when Clogging Occurs)

If clogging in the element cover 74 is detected by the above-described detection processes, heater control is performed to eliminate the clogging. Specifically, the heater 70 is operated for a long time to heat the element cover 74 to combust and remove foreign matter attached to the vent holes in the element cover 74 by heat from the heater 70. Preferably, in this heater control, the time for electric conduction through the heater 70 is set longer than the time for electric conduction through the heater 70 in the above-described PM combustion process so that the cover heating process can be carried out simultaneously with execution of the PM combustion process. Furthermore, the heater 70 forms cover heating means according to the present embodiment.

If the element cover 74 is subjected to clogging, the above-described cover heating process can quickly eliminate this state and recover the functions of the PM sensor 46. Moreover, the present embodiment enables the PM combustion process and the cover heating process to share the heater 70, allowing the structure of the sensor to be simplified. Furthermore, the PM combustion process and the cover heating process can be efficiently carried out at the same time. The illustrated configuration allows the heater 70 to heat the element cover 74. However, the present invention is not limited to this configuration. For example, besides the heater 70, a heater dedicated to the cover may be provided to heat the element cover 74.

Specific Processing Carried Out to Implement Embodiment 1

Figure 6:
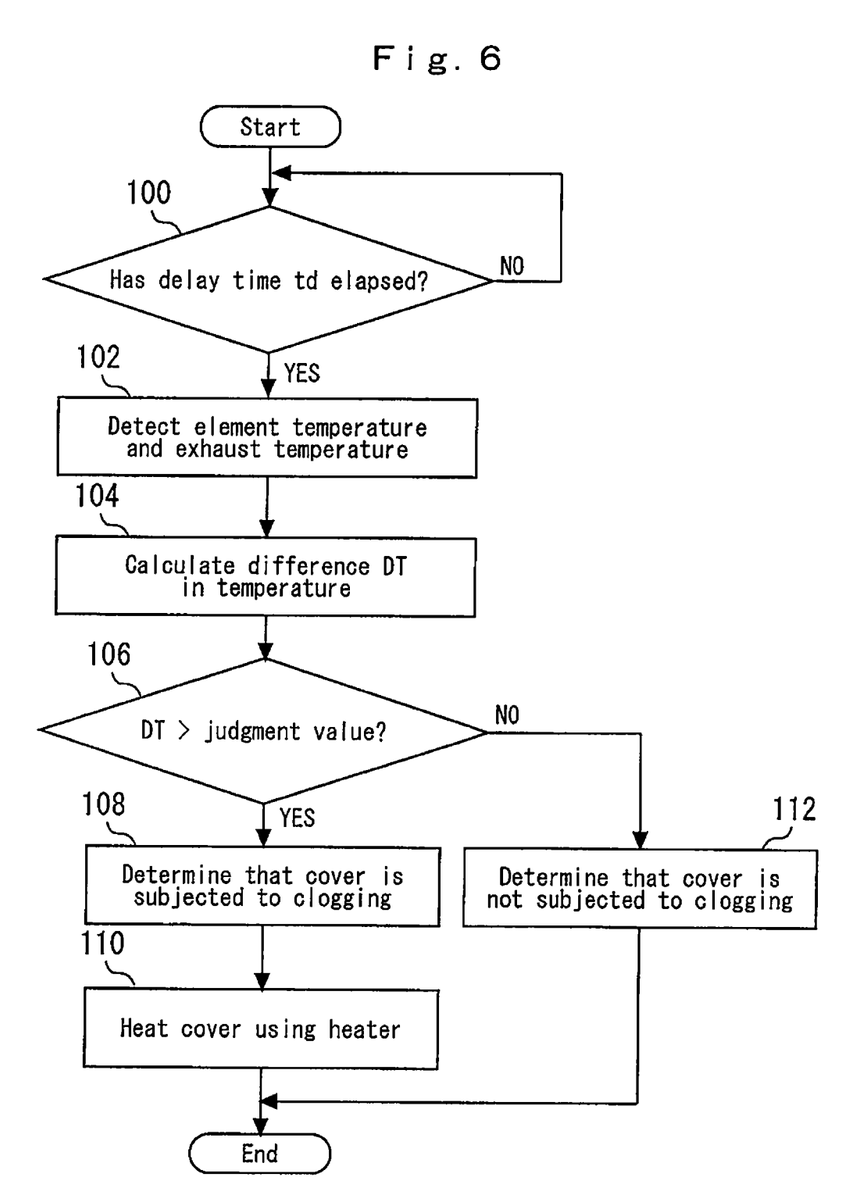
FIG. 6 is a flowchart showing the first clogging detection process carried out by the ECU according to Embodiment 1 of the present invention.
Figure 7:
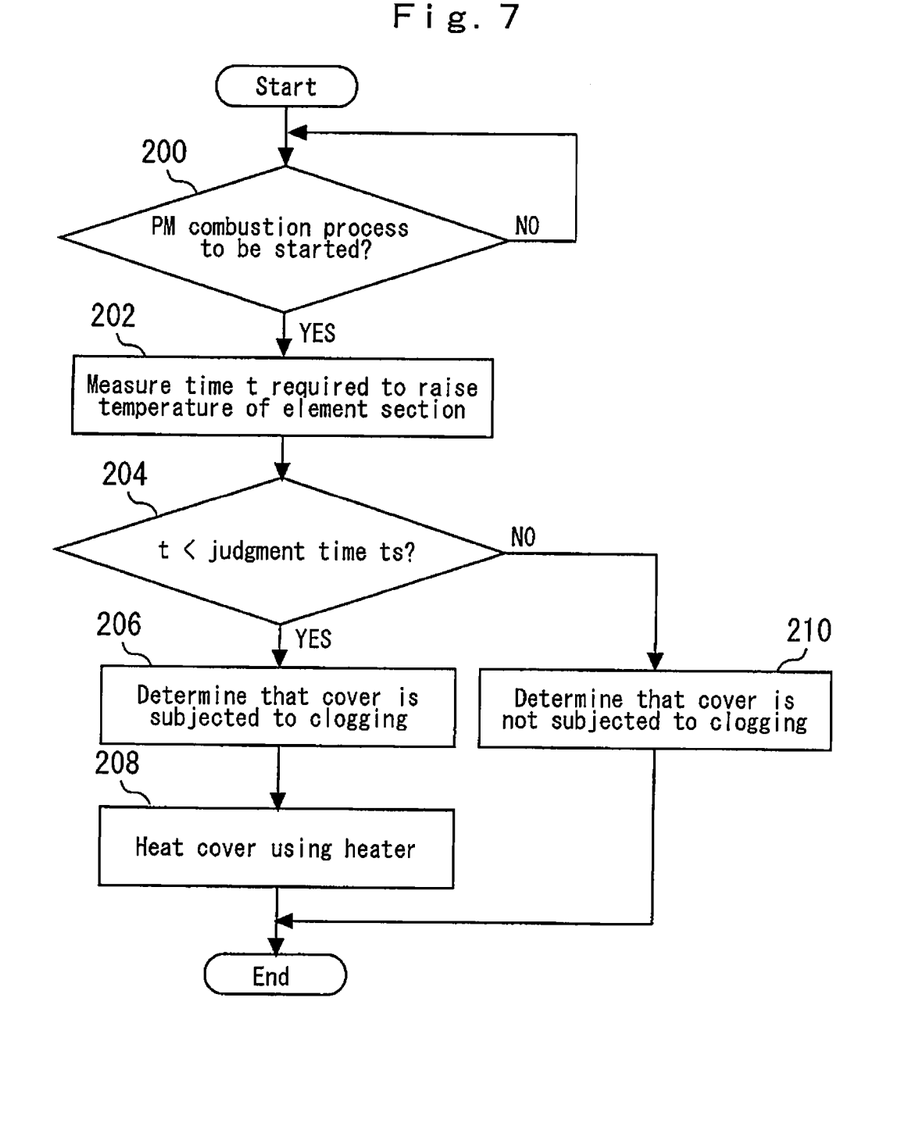
FIG. 7 is a flowchart showing the second clogging detection process carried out by the ECU according to Embodiment 1 of the present invention.

Now, with reference to FIG. 6 and FIG. 7, specific processing designed to implement the above-described control will be described. First, FIG. 6 is a flowchart showing the first clogging detection process carried out by the ECU according to Embodiment 1 of the present invention. A routine shown in FIG. 6 is assumed to be carried out, for example, when the engine is started. The routine shown in FIG. 6 first determines in step 100 whether or not a predetermined delay time td has elapsed. As shown in FIG. 4, the delay time td refers to the period when there is no great difference in the element temperature between the case where the element cover 74 is subjected to clogging and case where the element cover 74 is not subjected to clogging. During this period, determinations may be erroneous. Thus, if the determination in step 100 fails to be established, the routine waits until an affirmative determination is made.

Then, in step 102, the routine detects the element temperature and the exhaust temperature. In Step 104, the routine calculates the difference ΔT between the element temperature and the exhaust temperature. In step 106, the routine determines whether or not the difference ΔT is greater than the above-described judgment value. If this determination is affirmative, then in step 108, the routine determines that the element cover 74 is subjected to clogging. Then in step 110, the routine drives the heater 70 to carry out the above-described cover heating process. On the other hand, if the determination in step 106 is not affirmative, then in step 112, the routine determines that the element cover 74 is not subjected to clogging.

Now, with reference to FIG. 7, a second clogging detection process will be described. A routine shown in FIG. 7 is repeatedly carried out during operation of the engine and may be configured to be used together with the routine shown in FIG. 6. First, in step 200, the routine shown in FIG. 7 determines whether the PM combustion process has been started at the current timing. If this determination is not affirmative, the routine waits until an affirmative determination is made. Then in step 202, the routine measures the temperature rising time t of the element section 64. In step 204, the routine determines whether or not the temperature rising time t is shorter than the above-described judgment time ts. If this determination is affirmative, then in step 206, the routine determines that the element cover 74 is subjected to clogging. Then in step 208, the routine carries out the above-described cover heating process. On the other hand, if the determination in step 204 is not affirmative, then in step 210, the routine determines that the element cover 74 is not subjected to clogging.

In Embodiment 1 described above, step 106 shown in FIG. 6 is indicative of a specific example of clogging detection unit in the claims. Step 204 shown in FIG. 7 is indicative of a specific example of clogging detection unit in the claims. Steps 110 and 208 are indicative of a specific example of clogging elimination unit in the claims.

Furthermore, the embodiment illustrates the concomitant use of the first and second clogging detection processes. However, the present invention is not limited to this aspect and may be configured to use only one of the first and second clogging detection processes.

DESCRIPTION OF REFERENCE NUMERALS 10 engine, 12 piston, 14 combustion chamber, 16 crank shaft, 18 intake passage, 20 exhaust passage, 22 throttle valve, 24 DPF, 26 fuel injection valve, 28 suction valve, 30 exhaust valve, 40 crank angle sensor, 42 air flow sensor, 44 exhaust temperature sensor (exhaust temperature detection means), 46 PM sensor, 50 ECU, 62 element support section, 64 element section, 66 electrode, 68 element temperature detection section (element temperature detection means), 70 heater (cover heating means), 72 wire, 74 element cover

The invention claimed is:

1. A PM detection apparatus comprising:
an element section comprising at least two electrodes arranged opposite each other in a channel for exhaust gas, the element section being configured such that particulate matter in exhaust gas accumulates between the electrodes;
a detection processing section detecting an amount of the particulate matter contained in the exhaust gas based on a change in a value of resistance between the electrodes;
an element cover formed as a cover with a vent hole and covering the element section;
a heater heating the element section;
an element temperature detection unit for detecting a temperature of the element section; and
a clogging detection unit configured to detect when the vent hole in the element cover is clogged based on the temperature of the element section in a period of engine combustion from an initial state until a conductive path is formed between the electrodes by the particulate matter,
the clogging detection unit is configured to measure an elapsed time from a start of heating of the element section by the heater until the temperature of the element section reaches a predetermined reference temperature and configured to determine that the element cover is subjected to clogging if the elapsed time is shorter than a predetermined time.

2. A PM detection apparatus comprising:
an element section comprising at least two electrodes arranged opposite each other in a channel for exhaust gas, the element section being configured such that particulate matter in exhaust gas accumulates between the electrodes;
a detection processing section detecting an amount of the particulate matter contained in the exhaust gas based on a change in a value of resistance between the electrodes;
an element cover formed as a cover with a vent hole and covering the element section;
an element temperature detection unit for detecting a temperature of the element section;
an exhaust temperature detection unit for detecting an exhaust temperature on an upstream side of the element section; and
a clogging detection unit configured to detect when the vent hole in the element cover is clogged based on the temperature of the element section in a period of engine combustion from an initial state until a conductive path is formed between the electrodes by the particulate matter,
the clogging detection unit is configured to determine that the element cover is subjected to clogging if a difference obtained by subtracting the temperature of the element section from the exhaust temperature is greater than a predetermined judgment value.

3. The PM detection apparatus according to claim 1, wherein the clogging detection unit is configured to determine that the element cover is subjected to clogging if a change in the temperature of the element section observed when the element section is heated by the heater is greater than a predetermined judgment value.

4. The PM detection apparatus according to claim 1, comprising:
a clogging elimination unit for allowing the heater to heat the element cover to eliminate clogging if the clogging detection unit detects that the element cover is subjected to clogging.

5. The PM detection apparatus according to claim 2, comprising:
a clogging elimination unit for allowing a heater to heat the element cover to eliminate clogging if the clogging detection unit detects that the element cover is subjected to clogging.

6. The PM detection apparatus according to claim 1, wherein the period begins at an engine start.

7. The PM detection apparatus according to claim 2, wherein the period begins at an engine start.

8. A PM detection apparatus comprising:
an element section comprising at least two electrodes arranged opposite each other in a channel for exhaust gas, the element section being configured such that particulate matter in exhaust gas accumulates between the electrodes;
a detection processing section detecting an amount of the particulate matter contained in the exhaust gas based on a change in a value of resistance between the electrodes;
an element cover formed as a cover with a vent hole and covering the element section;
a heater heating the element section;
an element temperature detection unit for detecting a temperature of the element section; and
clogging detection processing circuitry configured to:
detect when the vent hole in the element cover is clogged based on the temperature of the element section in a period of engine combustion from an initial state until a conductive path is formed between the electrodes by the particulate matter, and to measure an elapsed time from a start of heating of the element section by the heater until the temperature of the element section reaches a predetermined reference temperature and configured to determine that the element cover is subjected to clogging if the elapsed time is shorter than a predetermined time.

9. A PM detection apparatus comprising:
an element section comprising at least two electrodes arranged opposite each other in a channel for exhaust gas, the element section being configured such that particulate matter in exhaust gas accumulates between the electrodes;
a detection processing section detecting an amount of the particulate matter contained in the exhaust gas based on a change in a value of resistance between the electrodes;
an element cover formed as a cover with a vent hole and covering the element section;
an element temperature detection unit for detecting a temperature of the element section;
an exhaust temperature detection unit for detecting an exhaust temperature on an upstream side of the element section; and
clogging detection processing circuitry configured to
detect when the vent hole in the element cover is clogged based on the temperature of the element section in a period of engine combustion from an initial state until a conductive path is formed between the electrodes by the particulate matter, and
determine that the element cover is subjected to clogging if a difference obtained by subtracting the temperature of the element section from the exhaust temperature is greater than a predetermined judgment value.

\* \* \* \* \*